(12) United States Patent
Adams et al.

(10) Patent No.: US 8,574,247 B2
(45) Date of Patent: Nov. 5, 2013

(54) SHOCK WAVE VALVULOPLASTY DEVICE WITH MOVEABLE SHOCK WAVE GENERATOR

(75) Inventors: John M. Adams, Snohomish, WA (US); Thomas G. Goff, Mountain View, CA (US)

(73) Assignee: Shockwave Medical, Inc., Fremont, CA (US)

( * ) Notice: Subject to any disclaimer, the term of this patent is extended or adjusted under 35 U.S.C. 154(b) by 0 days.

(21) Appl. No.: 13/291,875

(22) Filed: Nov. 8, 2011

(65) Prior Publication Data

US 2013/0116714 A1    May 9, 2013

(51) Int. Cl.
*A61B 17/22*    (2006.01)

(52) U.S. Cl.
USPC ..................................... 606/159; 604/101.01

(58) Field of Classification Search
USPC ................ 606/108, 159, 194; 623/1.11, 2.11; 604/96.01, 101.01
See application file for complete search history.

(56) References Cited

U.S. PATENT DOCUMENTS

| | | | |
|---|---|---|---|
| 3,785,382 A | 1/1974 | Schmidt et al. | |
| 4,662,126 A | 5/1987 | Malcolm | |
| 4,685,458 A | 8/1987 | Leckrone | |
| 5,009,232 A | 4/1991 | Hassler et al. | |
| 5,046,503 A | 9/1991 | Schneiderman | |
| 5,057,103 A | 10/1991 | Davis | |
| 5,078,717 A | 1/1992 | Parins et al. | |
| 5,152,767 A | 10/1992 | Sypal et al. | |
| 5,152,768 A | 10/1992 | Bhatta | |
| 5,176,675 A | 1/1993 | Watson et al. | |
| 5,195,508 A | 3/1993 | Muller et al. | |
| 5,246,447 A | 9/1993 | Rosen et al. | |
| 5,281,231 A | 1/1994 | Rosen et al. | |
| 5,295,958 A * | 3/1994 | Shturman | 604/103.07 |
| 5,324,255 A | 6/1994 | Passafaro et al. | |
| 5,368,591 A | 11/1994 | Lennox et al. | |
| 5,395,335 A | 3/1995 | Jang | |
| 5,417,208 A | 5/1995 | Winkler | |
| 5,425,735 A | 6/1995 | Rosen et al. | |
| 5,472,406 A | 12/1995 | de la Torre et al. | |
| 5,603,731 A | 2/1997 | Whitney | |
| 5,609,606 A | 3/1997 | O'Boyle | |
| 5,662,590 A | 9/1997 | de la Torre et al. | |
| 5,846,218 A | 12/1998 | Brisken et al. | |

(Continued)

FOREIGN PATENT DOCUMENTS

| | | |
|---|---|---|
| CN | 101043914 A | 9/2007 |
| EP | 0442199 A2 | 8/1991 |
| WO | 20091152352 A2 | 12/2009 |
| WO | 20101014515 A2 | 2/2010 |

OTHER PUBLICATIONS

Non Final Office Action received for U.S. Appl. No. 12/482,995, mailed on Jul. 12, 2013, 11 pages.

(Continued)

*Primary Examiner* — Victor Nguyen
(74) *Attorney, Agent, or Firm* — Morrison & Foerster LLP

(57) ABSTRACT

A valvuloplasty system includes a balloon adapted to be placed adjacent leaflets of a valve. The balloon is inflatable with a liquid. The system further includes a shock wave generator within the balloon that produces shock waves that propagate through the liquid for impinging upon the valve. The shock wave generator is moveable within the balloon to vary shock wave impingement on the valve.

10 Claims, 3 Drawing Sheets

(56) References Cited

U.S. PATENT DOCUMENTS

| | | | |
|---|---|---|---|
| 6,033,371 A | 3/2000 | Torre et al. | |
| 6,083,232 A | 7/2000 | Cox | |
| 6,113,560 A | 9/2000 | Simnacher | |
| 6,210,408 B1 | 4/2001 | Chandrasekaran et al. | |
| 6,277,138 B1 | 8/2001 | Levinson et al. | |
| 6,287,272 B1 | 9/2001 | Brisken et al. | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | de La Torre et al. | |
| 6,440,061 B1 * | 8/2002 | Wenner et al. | 600/114 |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 | 11/2003 | Rabiner et al. | |
| 6,736,784 B1 | 5/2004 | Menne et al. | |
| 6,755,821 B1 * | 6/2004 | Fry | 606/15 |
| 6,989,009 B2 | 1/2006 | Lafontaine | |
| 7,569,032 B2 | 8/2009 | Naimark et al. | |
| 8,162,859 B2 | 4/2012 | Schultheiss et al. | |
| 2001/0044596 A1 | 11/2001 | Jaafar | |
| 2002/0177889 A1 | 11/2002 | Brisken et al. | |
| 2004/0044308 A1 | 3/2004 | Naimark et al. | |
| 2004/0082859 A1 | 4/2004 | Schaer | |
| 2004/0249401 A1 | 12/2004 | Rabiner et al. | |
| 2005/0090846 A1 | 4/2005 | Pedersen et al. | |
| 2005/0171527 A1 | 8/2005 | Bhola | |
| 2005/0245866 A1 | 11/2005 | Azizi | |
| 2006/0004286 A1 | 1/2006 | Chang et al. | |
| 2006/0074484 A1 | 4/2006 | Huber | |
| 2006/0184076 A1 | 8/2006 | Gill et al. | |
| 2006/0190022 A1 * | 8/2006 | Beyar et al. | 606/192 |
| 2007/0129667 A1 | 6/2007 | Tiedtke et al. | |
| 2007/0239082 A1 | 10/2007 | Schultheiss et al. | |
| 2007/0239253 A1 | 10/2007 | Jagger et al. | |
| 2007/0244423 A1 | 10/2007 | Zumeris et al. | |
| 2007/0299481 A1 | 12/2007 | Syed et al. | |
| 2009/0254114 A1 | 10/2009 | Hirszowicz et al. | |
| 2009/0312768 A1 | 12/2009 | Hawkins et al. | |
| 2010/0016862 A1 | 1/2010 | Hawkins et al. | |
| 2010/0036294 A1 | 2/2010 | Mantell et al. | |
| 2010/0114020 A1 * | 5/2010 | Hawkins et al. | 604/101.01 |
| 2010/0121322 A1 | 5/2010 | Swanson | |
| 2010/0305565 A1 | 12/2010 | Truckai et al. | |
| 2011/0118634 A1 | 5/2011 | Golan | |
| 2011/0166570 A1 | 7/2011 | Hawkins et al. | |
| 2011/0295227 A1 | 12/2011 | Hawkins et al. | |
| 2012/0116289 A1 | 5/2012 | Hawkins et al. | |
| 2012/0221013 A1 | 8/2012 | Hawkins et al. | |
| 2013/0030431 A1 | 1/2013 | Adams | |
| 2013/0030447 A1 | 1/2013 | Adams | |

OTHER PUBLICATIONS

Extended European Search Report and Search Opinion received for EP Patent Application No. 098253933, mailed on Feb. 28, 2013, 6 pages.

International Search Report received for PCT Patent Application No. PCT/US2009/047070, mailed on Jan. 19, 2010, 4 pages.

International Preliminary Report on Patentability received for PCT Patent Application No. PCT/US2009/063354, mailed on May 19, 2011, 6 pages.

International Search Report received for PCT Patent Application No. PCT/US2009/063354, mailed on Jun. 11, 2010, 3 pages.

International Written Opinion received for PCT Patent Application No. PCT/US2009/063354, mailed on Jun. 11, 2010, 4 pages.

International Preliminary Report on Patentability received for PCT Patent Application No. PCT/US2011/047070, mailed on Feb. 21, 2013, 7 pages.

International Written Opinion received for PCT Patent Application No. PCT/US2011/047070, mailed on May 1, 2012, 5 pages.

International Preliminary Report on Patentability received for PCT Patent Application No. PCT/US2011/051606, issued on May 14, 2013, 6 pages.

International Search Report and Written Opinion received for PCT Patent Application No. PCT/US2011/051606, mailed on Apr. 24, 2012, 9 pages.

International Search Report received for PCT Patent Application No. PCT/US2012/023172, mailed on Sep. 28, 2012, 3 pages.

International Search Report received for PCT Patent Application No. PCT/US2012/063925, mailed on Mar. 25, 2013, 3 pages.

International Search Report and Written Opinion received for PCT Patent Application No. PCT/US2013/031805 mailed on May 20, 2013, 13 pages.

Adams et al., U.S. Appl. No. 13/534,658, filed Jun. 27, 2012, titled "Shock Wave Balloon Catheter with Multiple Shock Wave Sources".

Hakala et al., U.S. Appl. No. 13/831,543, filed Mar. 14, 2013, titled "Low Profile Electrodes for an Angioplasty Shock Wave Catheter", 52 pages.

Hawkins et al., U.S. Appl. No. 61/061,170, filed Jun. 13, 2008, titled "Shockwave Balloon Catheter System".

* cited by examiner

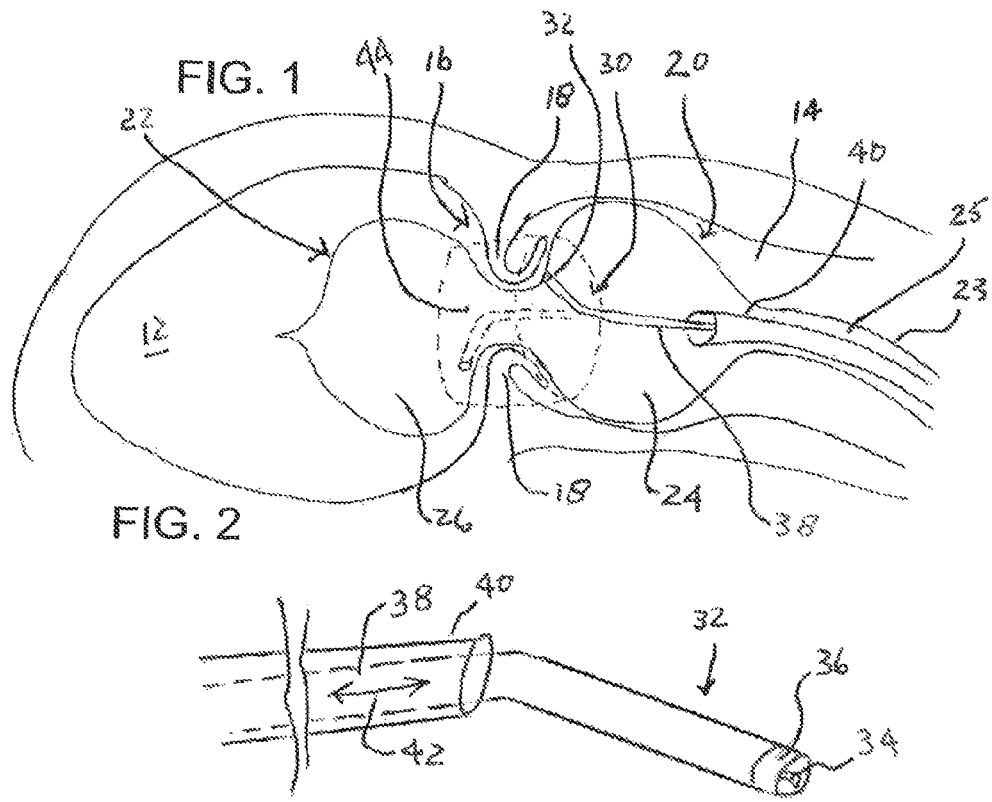
FIG. 1
FIG. 2
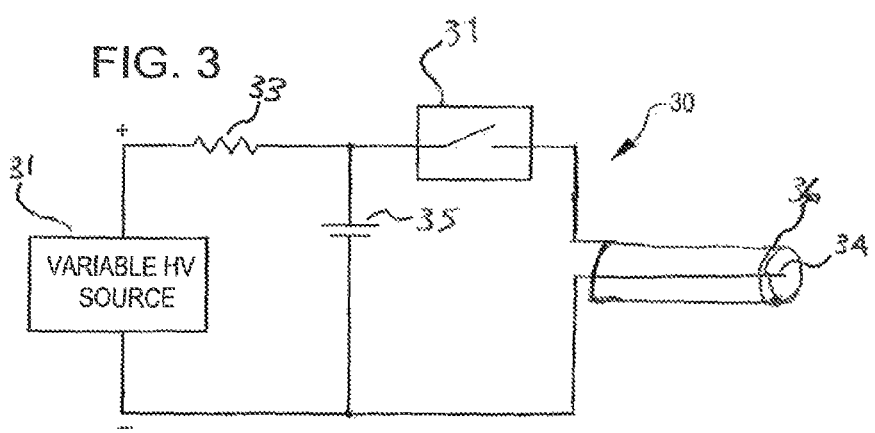
FIG. 3

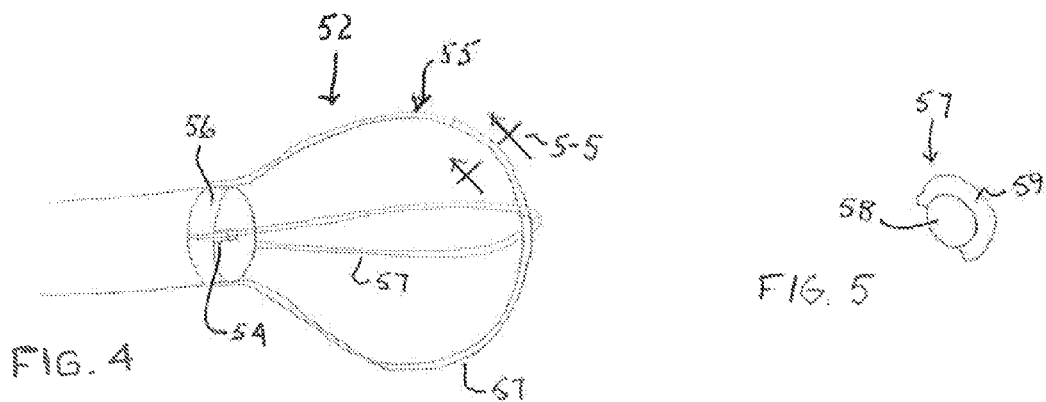
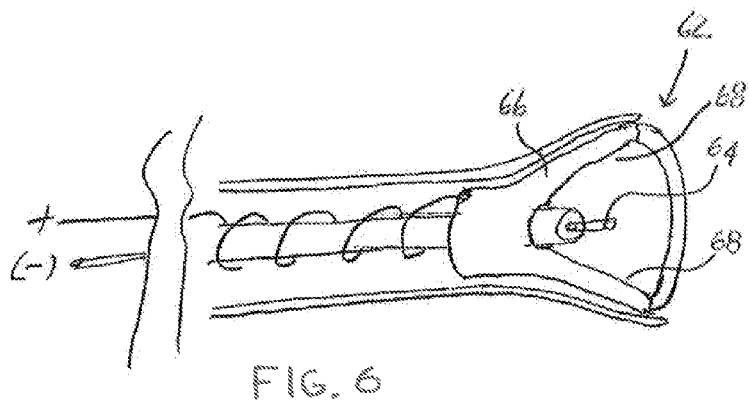
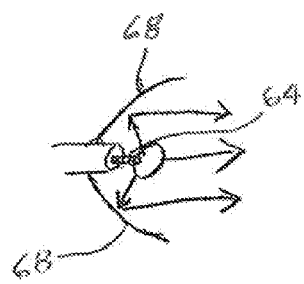

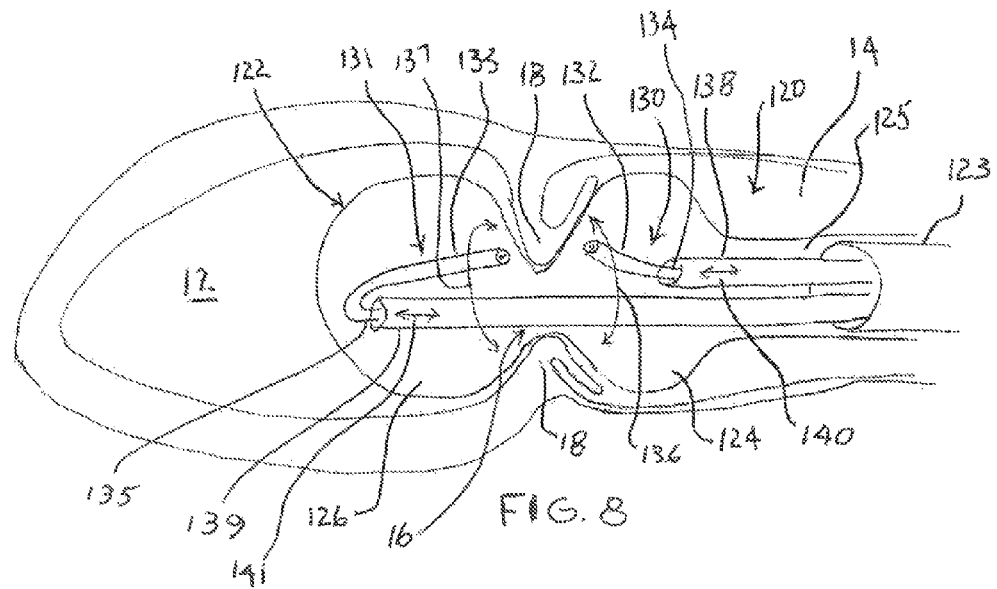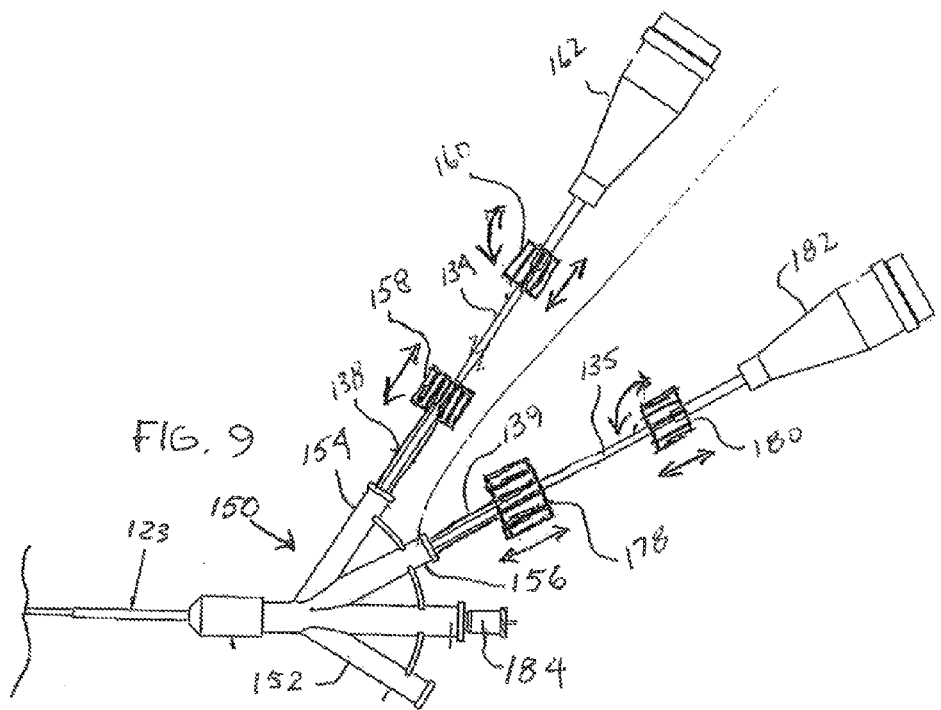

SHOCK WAVE VALVULOPLASTY DEVICE WITH MOVEABLE SHOCK WAVE GENERATOR

BACKGROUND OF THE INVENTION

Aortic calcification, also called aortic sclerosis, is a buildup of calcium deposits on the aortic valve in the heart. This often results in a heart murmur, which can easily be heard with a stethoscope over the heart. However, aortic calcification usually doesn't significantly affect the function of the aortic valve.

In some cases, though, the calcium deposits thicken and cause narrowing at the opening of the aortic valve. This impairs blood flow through the valve, causing chest pain or a heart attack. Doctors refer to such narrowing as aortic stenosis.

Aortic calcification typically affects older adults. But when it occurs in younger adults, it's often associated with an aortic valve defect that is present at birth (congenital) or with other illnesses such as kidney failure. An ultrasound of the heart (echocardiogram) can determine the severity of aortic calcification and also check for other possible causes of a heart murmur.

At present there is no specific treatment for aortic calcification. General treatment includes the monitoring for further developments of heart disease. Cholesterol levels are also checked to determine the need for medications to lower cholesterol in the hope to prevent progression of aortic calcification. If the valve becomes severely narrowed, aortic valve replacement surgery may be necessary.

The aortic valve area can be opened or enlarged with a balloon catheter (balloon valvuloplasty) which is introduced in much the same way as in cardiac catheterization. With balloon valvuloplasty, the aortic valve area typically increases slightly. Patients with critical aortic stenosis can therefore experience temporary improvement with this procedure. Unfortunately, most of these valves narrow over a six to 18 month period. Therefore, balloon valvuloplasty is useful as a short-term measure to temporarily relieve symptoms in patients who are not candidates for aortic valve replacement.

Patients who require urgent noncardiac surgery, such as a hip replacement, may benefit from aortic valvuloplasty prior to surgery. Valvuloplasty improves heart function and the chances of surviving non-cardiac surgery. Aortic valvuloplasty can also be useful as a bridge to aortic valve replacement in the elderly patient with poorly functioning ventricular muscle. Balloon valvuloplasty may temporarily improve ventricular muscle function, and thus improve surgical survival. Those who respond to valvuloplasty with improvement in ventricular function can be expected to benefit even more from aortic valve replacement. Aortic valvuloplasty in these high risk elderly patients has a similar mortality (5%) and serious complication rate (5%) as aortic valve replacement in surgical candidates.

Transarterial aortic valve replacement is a new procedure where the aortic valve is replaced with a self-expanding nitinol valve structure. Such procedures benefit from a smooth non-calcified circumference to attach the new valve. Large calcium deposits may induce leaks around the valve preventing a firm consistent attachment of the valve to the aorta. Thus there is a need for a calcium free valve bed to attach such self-expanding valves.

An alternative method and system for treating stenotic or calcified aortic valves is disclosed and claimed in co-pending U.S. application Ser. No. 12/611,997, filed Nov. 11, 2009 for SHOCKWAVE VALVULOPLASTY SYSTEM. As described therein, a balloon is placed adjacent leaflets of a valve to be treated and is inflatable with a liquid. Within the balloon is a shock wave generator that produces shock waves that propagate through the liquid and impinge upon the valve. The impinging shock waves soften, break and/or loosen the calcified regions for removal or displacement to open the valve or enlarge the valve opening.

The approach mentioned above provides a more tolerable treatment for aortic stenosis and calcified aortic valves than the previously performed aortic valve replacement. It is also a more effective treatment than current valvuloplasty therapy. For patients undergoing transaortic or catheter based aortic valve replacement, this new method can soften, smooth, and open the aortic valve annulus more effectively than current valvuloplasty and prepare the area for a catheter delivered valve.

In the shock wave valvuloplasty described above, the impingement intensity of the shockwaves diminishes as a function of the distance from the shock wave origination point to the valve. More specifically, the impingement intensity of the shock waves is inversely proportional to the square of the distance from the shock wave origination point to the valve. Hence, when applying the shock waves, it would be desirable to maximize their effectiveness by being able to minimize the distance between the shock wave source and the valve location being treated at that moment. The present invention address this and other matters of importance in providing the most efficient and effective treatment possible.

SUMMARY OF THE INVENTION

According to one embodiment, a valvuloplasty system comprises a balloon adapted to be placed adjacent leaflets of a valve. The balloon is inflatable with a liquid. The system further includes a shock wave generator within the balloon that produces shock waves that propagate through the liquid for impinging upon the valve. The shock wave generator is moveable within the balloon to vary shock wave impingement on the valve.

The shock wave generator may be moveable within the balloon to subscribe a circular area. The shock wave generator may further be moveable within the balloon to subscribe a cylindrical space.

The shock wave generator includes at least one electrode.

The system may further comprise an elongated element that carries the at least one electrode to extend into the balloon and an elongated sheath through which the elongated element extends. The at least one electrode may be moveable within the balloon by displacement of the elongated element and/or the sheath. The at least one electrode may be moveable within the balloon to subscribe a circular area and may be further moveable within the balloon to subscribe a cylindrical space.

The system may further comprise an elongated carrier with the balloon being at one end of the carrier in sealed relation thereto. The system may further comprise an elongated element that carries the at least one electrode to extend through the carrier into the balloon. The at least one electrode may be moveable within the balloon to subscribe a circular area by rotational displacement of the elongated element and may be further moveable within the balloon to subscribe a cylindrical space by rotational and axial displacement of the elongated element.

The carrier has a distal end and a proximal end and the elongated element has a distal end and a proximal end. The balloon may be at the distal end of the carrier and the at least one electrode may be at the distal end of the elongated element so that the elongated element may extend through the carrier from the balloon to the proximal end of the carrier and the elongated element may be displaceable at the proximal end of the carrier.

The system may further include an elongated sheath through which the elongated element and the at least one electrode extend. The size of the circular area subscribed by the at least one electrode within the balloon may be adjustable by axial displacement of the elongated element with respect to the sheath. To that end, the at least one electrode may extend from the elongated element at an angle. The at least one electrode and the elongated element are formed from a common conductor.

The system may further comprise a cage enclosing the at least one electrode that prevents the at least one electrode from contacting the balloon. The cage may be formed of electrically insulative material. Alternatively, the cage may be formed of conductive material and include an insulation covering at least a portion of the cage. The shock wave generator may further include a second electrode within the balloon. The cage may form the second electrode.

The shock wave generator may further include a reflector that directs the shockwaves generated by the at least one electrode in a desired direction. The reflector may be arranged to move with the at least one electrode.

The at least one electrode may comprise an electrode pair.

The electrode pair are formed by coaxially disposed electrodes including a center electrode and an outer electrode circumscribing the center electrode. The shock wave generator may further include a reflector carried by the electrode pair that directs the shockwaves in a desired direction. The reflector may be coupled to the outer electrode.

The shock wave generator may further include a pulsating voltage source. The pulsating voltage source may be arranged to provide the at least one electrode with a negative polarity.

The balloon may comprise first and second chambers and the shock wave generator may comprise the at least one electrode within the first chamber and a second electrode within the second chamber. The at least one electrode may be moveable within the first chamber and the second electrode may be moveable within the second chamber. Each of the at least one electrode and the second electrode may be arranged for movement to subscribe a cylindrical space.

Each of the at least one electrode and the second electrode may comprise a first electrode pair and a second electrode pair, respectively. The first and second electrode pair may each be formed by coaxially disposed electrodes including a center electrode and an outer electrode circumscribing the center electrode.

One of the at least one electrode and the second electrode may be a distal electrode with respect to the other one of the at least one electrode and second electrode. The distal electrode may be moveable axially so as to be proximal to the other one of the at least one electrode and second electrode.

One of the at least one electrode and the second electrode may be a distal electrode with respect to the other one of the at least one electrode and second electrode. The distal electrode may be reflexed in a proximal direction.

According to another embodiment, a valvuloplasty system for treating a calcified valve comprises an elongated carrier, a balloon at one end of the carrier in sealed relation thereto, the balloon being inflatable with a liquid and including a first chamber and a second chamber, and a shock wave generator including a first electrode within the balloon first chamber and a second electrode within the balloon second chamber. The electrodes are arranged to produce shock waves within their respective balloon chambers that propagate through the liquid and impinge upon the valve being treated adjacent the balloon chambers. The first electrode is moveable within the first balloon chamber and the second electrode is moveable within the second balloon chamber.

The shock wave generator further includes a pulsating voltage source. The pulsating voltage source is arranged to provide the first and second electrodes with a negative polarity. Each of the first and second electrodes is moveable within its respective balloon chamber to subscribe a cylindrical space.

The system may further comprise a first drive element coupled to the first electrode and a second drive element coupled to the second electrode. The first and second electrodes may each be arranged to subscribe a cylindrical space by rotational and longitudinal displacement of their respective drive element.

Each of the first electrode and the second electrode may comprise a first electrode pair and a second electrode pair, respectively. The first and second electrode pair may each be formed by coaxially disposed electrodes including a center electrode and an outer electrode circumscribing the center electrode.

One of the at least one electrode and the second electrode may be a distal electrode with respect to the other one of the at least one electrode and second electrode. The distal electrode may be moveable axially so as to be proximal to the other one of the at least one electrode and second electrode.

The distal electrode may be reflexed in a proximal direction.

According to another embodiment, a valvuloplasty method for treating a cardiac valve comprises the steps of placing a balloon adjacent to the valve, inflating the balloon with a liquid, and introducing a shock wave generator into the balloon arranged to produce shock waves within the balloon to propagate through the liquid for impinging upon the valve. The method further includes the steps of producing shock waves within the balloon with the shock wave generator and changing the position of the shock wave generator within the balloon to vary the shock wave impingement upon the valve.

The shock wave generator may include at least one electrode and the producing step may include applying pulsating electrical energy to the at least one electrode. The step of changing the position of the shock wave generator within the balloon may include moving the at least one electrode along an arcuate path.

The arcuate path has a radius of curvature and the step of changing the position of the shock wave generator within the balloon may further include varying the radius of curvature.

The step of changing the position of the shock wave generator within the balloon may include moving the at least one electrode longitudinally within the balloon. The step of changing the position of the shock wave generator within the balloon may include moving the at least one electrode within a subscribed cylindrical space. The method may include the further steps of introducing a second shock wave generator into the balloon arranged to produce shock waves within the balloon to propagate through the liquid for impinging upon the valve, producing shock waves within the balloon with the second shock wave generator, and changing the position of the second shock wave generator within the balloon to vary the shock wave impingement upon the valve.

BRIEF DESCRIPTION OF THE DRAWINGS

The features of the present invention which are believed to be novel are set forth with particularity in the appended claims. The various described embodiments of the invention, together with representative features and advantages thereof, may best be understood by making reference to the following description taken in conjunction with the accompanying drawings, in the several figures of which like reference numerals identify identical elements, and wherein:

FIG. 1 is a cut away view of an aortic valve of a heart with a treatment balloon placed on both sides of the aortic valve leaflets, according aspects of the present invention;

FIG. 2 is a partial perspective view of an electrode pair which may be employed as a shock wave generator within the treatment balloon of FIG. 2 according to aspects of the invention;

FIG. 3 is a simplified schematic diagram of a valvuloplasty system according to aspects of the invention;

FIG. 4 is a partial perspective view of another electrode pair which may be employed as a shock wave generator within the treatment balloon of FIG. 2 according to further aspects of the invention;

FIG. 5 is a sectional view taken along lines 5-5 of FIG. 4;

FIG. 6 is a partial perspective view of an electrode pair which may be employed as a shock wave generator within the treatment balloon of FIG. 2 that includes a reflector that reflects and focuses the shock waves in a desired direction according to further aspects of the invention;

FIG. 7 is simplified side view illustrating the operation of the reflector of FIG. 6;

FIG. 8 is a cut away view of an aortic valve of a heart with another treatment balloon placed on both sides of the aortic valve leaflets at the distal end of a valvuloplasty system, according to further aspects of the present invention; and FIG. 9 is a plan view of the proximal end of the valvuloplasty system of FIG. 8.

DETAILED DESCRIPTION OF THE INVENTION

Referring now to FIG. 1, it is a cut away view of an aortic valve 16 of a heart with a treatment balloon 22 placed on both sides of the aortic valve leaflets 18. Also shown are the left ventricle 12 and the aorta 14 of the heart. Valves of the heart, such as the aortic valve 16 can become stenotic and calcified. More particularly, the opening of the valve defined by the leaflets can become stenotic and calcified. This can restrict the size of the opening as the valve leaflets 18 are thickened with calcium deposits and fibrotic tissue. The thickened leaflets 18 and smaller valve opening restrict blood flow from the heart creating excess work for the heart and poor cardiac output. As previously mentioned, current treatment includes replacement of the valve or attempts to stretch the valve annulus with a balloon.

FIG. 1 also shows a valvuloplasty system 20 embodying aspects of the present invention within the aortic valve 16 to treat the stenotic and calcified valve 16. The system 20 includes a treatment balloon 22 and a shock wave generator 30. The balloon 22 includes two longitudinally spaced chambers 24 and 26 placed on opposed sides of the aortic valve leaflets 18. The balloon 22 may be formed from a compliant or a non-compliant material. The balloon is at the distal end of a carrier formed by an elongated tube 23. The two longitudinally spaced chambers 24 and 26 share a common inflation lumen 25 of the tube 23 to permit the balloon 22 to be filled with a liquid, such as saline. Alternatively the balloon chambers 24 and 26 may not share the same inflation fluid path.

The shock wave generator 30 includes at least one electrode that produces electrical arcs within the balloon to produce shock waves within the confined liquid. The shock waves propagate through the liquid and impinge upon the balloon wall and the valve. The impinging shock waves cause the calcified material on the valve to break and/or soften. This permit the valve opening to be widened or the calcified material to be removed.

In accordance with the embodiment of FIG. 1, the shock wave generator 30 includes an electrode pair 32. Such an electrode pair 32 is shown in greater detail in FIG. 2, to which attention is temporarily drawn. The electrode pair 32 includes a first electrode 34 and a second electrode 36. The electrodes are coaxially disposed with electrode 34 being a center electrode and electrode 36 being an outer electrode circumscribing the center electrode 34. The electrode pair 32 are carried by an integral elongated element or extension 38 that may extend back to the proximal end of the system 20. The elongated element 38 is thus formed by both extensions of the center electrode 34 and the outer electrode 36. As may be noted in FIG. 1, the electrode pair 32 is offset from the element 38 at an angle. As a result, rotation of the element 38 causes the electrode pair to subscribe a circular area. Further, the element extends down a sheath 40 which in turn may also extend back to the proximal end of the system 20. The element 38 and the sheath 40 are axially displaceable within the balloon and with respect to each other as indicated by arrows 42 at the proximal end of the system. As the element 38 is displaced axially in the proximal direction with respect to the sheath 38, the electrode pair 32 is drawn further into the sheath 40 and deflected to a lesser extent to subscribe a circular area of smaller radius. Conversely, as the element 38 is displaced axially in the distal direction with respect to the sheath 38, the electrode pair 32 is extended further out of the sheath 40 and deflects to a greater extent to subscribe a circular area of larger radius.

Because the sheath 40 and the element 38 are axially displaceable within the tube 23, the electrode pair 32 may be moved axially within the balloon chambers 24 and 26. The axial movement of the electrode pair 32 together with the rotational movement of the element 38 causes the electrode pair 32 to subscribe a cylindrical space represented in dashed lines and designated with reference numeral 44 in FIG. 1. This movement of the electrode pair 32 permits the electrode pair 32 to be used to treat the valve 16 in both balloon chambers 24 and 26 and on both sides of the leaflets 18. It also permits the shock waves produced by the electrode pair to be directed towards specific areas of the valve 16 to enhance treatment and to vary the intensity of the shock wave impingement on the valve 16.

FIG. 3 is a simplified schematic diagram of the shock wave generator 30. It includes a high voltage power supply 31, a series resistance 33, a capacitance 35, and a high voltage switch 37. The voltage needed to form the electrical arc will depend on the gap between the electrodes 34 and 36 and may range between 100 to 3000 volts, for example. The high voltage switch 37 can be set to control the duration of the pulses applied to the electrodes. The pulse duration will depend on the surface area of the electrodes 34 and 36 and needs to be sufficient to generate a gas bubble at the surface of the electrode causing a plasma arc of electric current to jump the bubble and create a rapidly expanding and collapsing bubble, which creates the shock wave in the balloon. Such shock waves can be as short as a few microseconds. It may be noted in FIG. 3, that the negative terminal of the power supply 31 is connected to the center electrode 34. Also, the shock waves may be synchronized to the R wave of the heart in a manner as described for example in co-pending application Ser. No. 61/061,170 filed on Jun. 13, 2008, which application is incorporated herein in its entirety. Thus, the high voltage pulses within the shock wave generator 30 are applied to the electrode pairs 34 and 36 in a manner as described in the aforementioned application Ser. No. 61/061,170 to create shockwaves within the fluid within the balloon 22. The shock waves impinge upon the valve leaflets 18 and the valve annulus to cause the break-up of calcium deposits and fibrotic tissue on the valve leaflets 18 and annulus to open and smooth the aortic valve 16.

Referring now to FIG. 4, it is a partial perspective view of another electrode pair which may be employed as a shock wave generator within the treatment balloon of FIG. 1 according to further aspects of the invention. Here, the electrode pair 52 includes a center electrode 54 and an outer electrode 56. As in the previous embodiment, the outer electrode 56 circumscribes the inner electrode 54. The electrode pair 52 further includes a cage 55 that is carried by the outer electrode 56. The cage 55 includes a plurality of elements 57 that enclose the inner electrode 54 to protect the inner electrode from contacting the inner surface of the balloon 22. As may be noted in the sectional view of FIG. 5, the cage elements 57 may be formed of conductive wire 58 covered at least in part with an insulator 59. Alternatively, the cage elements may be form entirely of a non-conductor material.

FIG. 6 is a partial perspective view of a further electrode pair which may be employed as a shock wave generator within the treatment balloon of FIG. 1 according to further aspects of the invention. Here, the electrode pair 62 includes a center electrode 64 and an outer electrode 66. The outer electrode 66 takes the form of a reflector 68. As shown in FIG. 7, the reflector 68 provides a narrowed envelope of shock wave energy and directs the shock waves in a desired direction. The concentration of the shock wave energy provided by the reflector further contributes towards the provision of shock wave energy sufficient to soften or break the calcified regions of the valve being treated. The reflector 68, by being a part of the outer electrode 66, is moveable with the electrode pair 62. This makes the direction and concentration of the shock wave energy convenient to control. Also, the center electrode 64 is shown connected to the negative side of the power supply. It has been observed that the bubble causing the shock waves emanate from the negative electrode. The reflector 68 by enveloping the electrode 64 from which the shock wave bubble emanates provides uniform control and distribution of the shock wave energy within the narrowed envelope of energy. As in the previous embodiment, the reflector may also serve to protect the center electrode 64 from contacting the inner surface of the balloon 22.

FIG. 8 is a cut away view of another valvuloplasty system 120 embodying the present invention. The system includes a treatment balloon 122 deployed on both sides of the leaflets 18 of an aortic valve 16. The balloon 122 may be formed from a compliant or a non-compliant material. The balloon, as seen in FIG. 8, is at the distal end of a carrier formed by an elongated tube 123. The treatment balloon 122 has two longitudinally spaced chambers 124 and 126 that share a common inflation lumen 125 of the tube 123. Alternatively the balloon chambers 124 and 126 may not share the same inflation fluid path. The chambers 124 and 126 are longitudinally spaced such that chamber 124 is positioned on one side of the aortic valve leaflets 18 and chamber 126 is positioned on the other side of the aortic valve leaflets 18. The chambers 124 and 126 may be inflated with saline/contrast mixture, for example.

The system 120 further includes a shockwave generator 130 shown within balloon chamber 124 and a shock wave generator 131 shown within balloon chamber 126. Each of the shock wave generators includes an electrode pair. To that end, shock wave generator 130 includes electrode pair 132 and shock wave generator 131 includes electrode pair 133. The electrode pairs 132 and 133 may take the form of any one of the electrode pairs previously described.

As in the previous embodiment, the shock wave pairs 132 and 133 are carried by respective integral elongated elements 134 and 135. It is of course not required that the elongated elements be integral with their respective electrode pairs. The elongated elements 134 and 135 extend through sheaths 138 and 139 respectively to the proximal end of the system 120. The elongated elements 134 and 135 are each rotatable as indicated enable their respective electrode pairs 132 and 133 to subscribe a circular area as indicate by arrows 136 and 137. Further, the sheaths 138 and 139 are axially within the carrier 123 and balloon 122 as indicated by arrows 140 and 141. Still further, the elongated elements 134 and 135 are axially moveable within their respective sheaths 138 and 139. As a result, the electrode pairs 132 and 133 are afforded three dimensional freedom of movement to subscribe cylindrical space.

The shock wave generators 130 and 131 may be active to generate shock waves either together are individually. If it becomes necessary to rotate the proximal electrode pair 132, the electrode pair 133 may first be moved proximally by axial movement of its sheath 139 so that it is proximal to electrode pair 132 and out of the way. As may be further noted in FIG. 8, the distal electrode pair 133 is reflexed in the proximal direction pointing towards the distal side of the leaflets 18. This provides more direct access to the aortic valve 16 by the electrode pair 133. To this end, shockwave generator 131 has a preformed shape defining a 180 degree bend. It assumes this shape to reflex electrode pair 133 when it extends out of sheath 139.

As may be seen from the above, the valvuloplasty system 120 of FIG. 8 provides the physician with many degrees of freedom for accessing the aortic valve with the shock wave generators 130 and 131. The movement of the shock wave generators 130 and 131 enabled by this embodiment permits the physician to adjust the distance of the shock wave generators from the valve 16 and the approach angle to the valve 16 in order to maximize the available shock wave energy. It also enables the gentle softening and breaking of the calcified regions of an anatomical feature that is difficult reach and fully access.

Referring now to FIG. 9, it is a plan view of the proximal end of the valvuloplasty system 120 of FIG. 8. Here it may be seen that the proximal end of the system 120 terminates in a yoke assembly 150. The yoke assembly 150 is connected to the carrier 123 and includes a fill port 152 to permit the inflation fluid, such as saline, into the inflation lumen 125 (FIG. 8) of the carrier 123. The yoke has extensions 154 and 156 associated with the shock wave generators 130 and 131 respectively. Each extension accommodates controls for axially displacing the sheaths and for axially displacing and rotating the elongated elements that extend through the sheaths and carry the electrode pairs of the shock wave generators. Hence, the proximal end of the system 120 has a control knob 158 for controlling the axial displacement of sheath 138 of shock wave generator 130 and a control knob 160 for controlling the axial displacement and rotation of the elongated element 134 of shockwave generator 130. An electrical connector 162 provides electrical connections to the electrode pair 132 of shock wave generator 130. Similarly, the proximal end of the system 120 has another control knob 178 for controlling the axial displacement of sheath 139 of shock wave generator 131 and a control knob 180 for controlling the axial displacement and rotation of the elongated element 135 of shockwave generator 131. An electrical connector 182 provides electrical connections to the electrode pair 133 of shock wave generator 131. As a result, complete control of the sheaths, the elongated elements, and hence the electrode pairs is afforded at the proximal end of the system 120. Given the metallic nature of electrode pair 132 and 133, their position can be observed with fluoroscopy as is well known.

The extension further includes a guide wire port 184 for receiving a guide wire. The guide wire serves to feed the system into place in a manner known in the art. The guide wire has not been shown to avoid undue complication.

While particular embodiments of the present invention have been shown and described, modifications may be made, and it is therefore intended to cover all such changes and modifications which fall within the true spirit and scope of the invention.

What is claimed is:

1. A valvuloplasty method for treating a cardiac valve, comprising:
    placing a balloon adjacent to the valve, wherein the balloon has a longitudinal axis;
    inflating the balloon with a liquid;
    introducing a shock wave generator into the balloon at a first location, wherein the shock wave generator is arranged to produce a shock wave within the balloon to propagate through the liquid for impinging upon the valve, and wherein the shock wave generator is mounted on an elongate element that is slidably enclosed within an elongate tube;
    initiating a shock wave within the balloon from the first location;
    changing the position of the shock wave generator within the balloon to a second location that is axially and/or longitudinally displaced from the first location; and
    initiating a shock wave within the balloon from the second location to vary the shock wave impingement upon the valve.

2. The method of claim 1, wherein the shock wave generator includes at least one electrode, and wherein initiating a shock wave includes applying pulsating electrical energy to the at least one electrode.

3. The method of claim 2, wherein the step of changing the position of the shock wave generator within the balloon includes moving the at least one electrode along an arcuate path.

4. The method of claim 3, wherein the arcuate path has a radius of curvature, and wherein the step of changing the position of the shock wave generator within the balloon further includes varying the radius of curvature.

5. The method of claim 2, wherein the step of changing the position of the shock wave generator within the balloon includes moving the at least one electrode longitudinally within the balloon.

6. The method of claim 2, wherein the step of changing the position of the shock wave generator within the balloon includes moving the at least one electrode within a subscribed cylindrical space.

7. The method of claim 1, further comprising the steps of introducing a second shock wave generator into the balloon arranged to produce a shock wave within the balloon to propagate through the liquid for impinging upon the valve, initiating a shock wave within the balloon with the second shock wave generator from a third location, changing the position of the second shock wave generator within the balloon to a fourth location that is axially and/or longitudinally displaced from the third location, and initiating a shock wave within the balloon with the second shock wave generator from the fourth location.

8. The method of claim 1, wherein an axial distance from the first location to the longitudinal axis of the balloon is different from an axial distance from the second location to the longitudinal axis of the balloon.

9. The method of claim 1, wherein the second location is longitudinally displaced from the first location.

10. The method of claim 1, wherein a distal portion of the elongate element has a pre-shaped bend, and wherein the step of changing the position of the shock wave generator includes advancing or retracting the elongate element within the elongate tube so that the second location of the shockwave generator is both longitudinally and axially displaced from the first location.

\* \* \* \* \*